Figure 1:
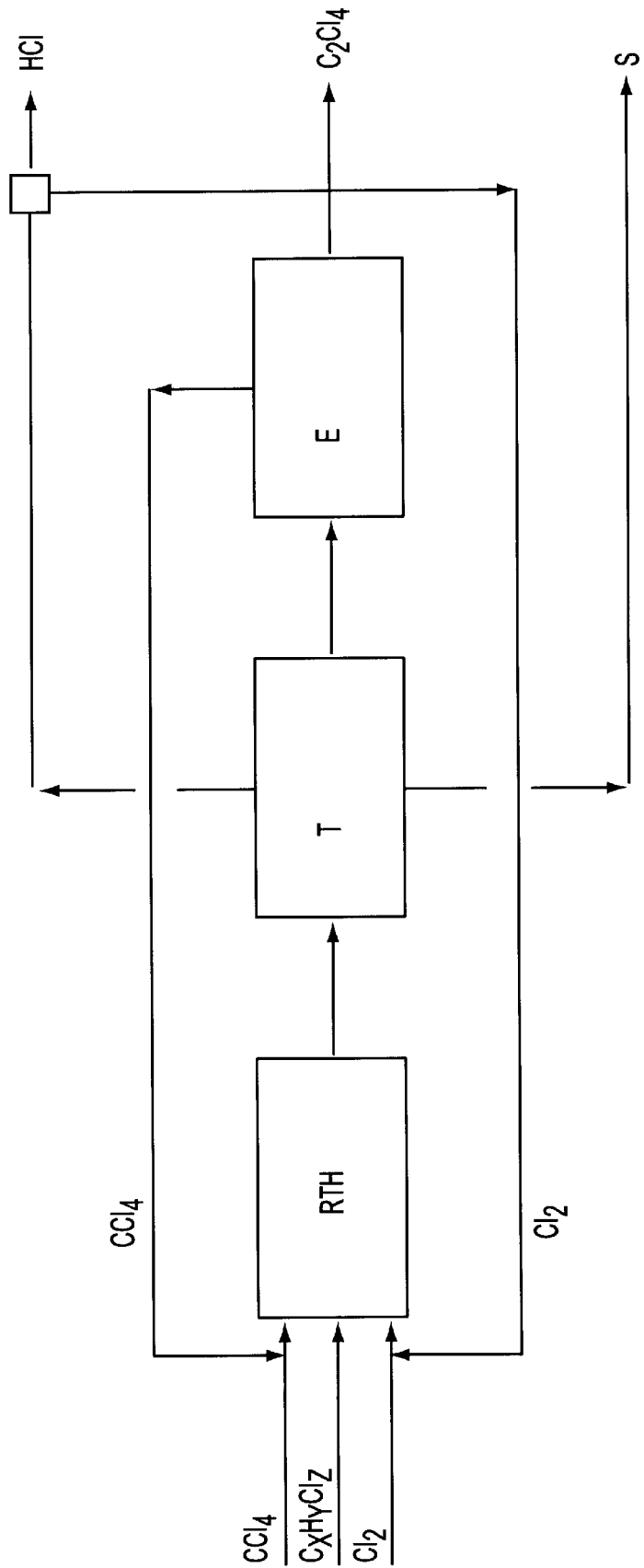

United States Patent [19]
Monzain et al.

[11] Patent Number: 6,060,630
[45] Date of Patent: May 9, 2000

[54] PROCESS FOR THE PRODUCTION OF PERCHLOROETHYLENE

[75] Inventors: Michel Monzain, Triel/Seine; Eric Bouilhot, Tavaux, both of France

[73] Assignee: Solvay (Societe Anonyme), Brussels, Belgium

[21] Appl. No.: 09/210,909

[22] Filed: Dec. 15, 1998

[30] Foreign Application Priority Data

Dec. 15, 1997 [FR] France .................................. 97.16050

[51] Int. Cl.$^7$ .................................................. C07C 17/38
[52] U.S. Cl. ............................................ 570/237; 570/218
[58] Field of Search ..................................... 570/237, 218

[56] References Cited

U.S. PATENT DOCUMENTS 5,426,256   6/1995   Petrosky .

FOREIGN PATENT DOCUMENTS

0573920A2  12/1993  European Pat. Off. .
2.120.81    8/1972   France .
1366221     9/1974   United Kingdom .

*Primary Examiner*—Alan Siegel
*Attorney, Agent, or Firm*—Venable

[57] ABSTRACT

The present invention relates to a process for the production of perchloroethylene by non-catalytic thermal chlorination of hydrocarbons, of partially chlorinated hydrocarbons and/or of mixtures thereof, combined with the conversion into perchloroethylene of $CCl_4$ obtained from external sources.

15 Claims, 2 Drawing Sheets

PROCESS FOR THE PRODUCTION OF PERCHLOROETHYLENE

The present invention relates to a process for the production of perchloroethylene by non-catalytic thermal chlorination of hydrocarbons, of partially chlorinated hydrocarbons and/or of mixtures thereof, combined with the conversion into perchloroethylene of carbon tetrachloride (CCl$_4$) obtained from external sources.

During the manufacture of perchloroethylene by thermal chlorination of hydrocarbons or of partially chlorinated hydrocarbons, large amounts of CCl$_4$ are generally obtained as a by-product. However, following the Montreal Protocol, the industrial use of carbon tetrachloride is greatly limited.

It is known that, depending on the operating conditions, the reaction can be directed either towards the production of carbon tetrachloride or towards the production of perchloroethylene. The following equilibrium reaction is known between carbon tetrachloride and perchloroethylene:

$$2CCl_4 = C_2Cl_4 + 2Cl_2 \qquad (1)$$

However, the production of perchloroethylene from carbon tetrachloride via the reaction (1) is generally accompanied by the formation of large amounts of high-boiling by-products, such as hexachlorobenzene.

Patent application EP 0,573,920 proposes a process for the production of perchloroethylene from hydrocarbons and/or from partially chlorinated hydrocarbons, from chlorine and from carbon tetrachloride in a reaction plant maintained at a temperature of between 500° C. and 700° C. and at a pressure of 100–200 kPa in order to obtain a gas in which the amount of CCl$_4$ is less than the amount of CCl$_4$ injected and in which the concentration of chlorine is between 7 and 15 mol %. The chlorine and the CCl$_4$ contained in the gas produced are recycled according to the process. However, this process does not make it possible to convert large amounts of external CCl$_4$, i.e. of CCl$_4$ not generated in the process.

U.S. Pat. No. 5,426,256 describes a similar process in which the reagents are introduced into a reaction plant via a premixing zone. In that process, the carbon tetrachloride must be partly introduced in liquid form and partly in gaseous form.

The aim of the present invention is to propose a process for the production of perchloroethylene by non-catalytic chlorination which makes it possible to convert large amounts of external carbon tetrachloride, without generating large amounts of by-products such as hexachlorobenzene, and which avoids the drawbacks of the previous processes.

To this end, the invention relates to a process for the production of perchloroethylene by non- catalytic thermal chlorination of hydrocarbons, of partially chlorinated hydrocarbons and/or of mixtures thereof, combined with the conversion into perchloroethylene of carbon tetrachloride obtained from external sources, the process comprising the following steps:

a) production of perchloroethylene by passing carbon tetrachloride, C$_1$–C$_3$ hydrocarbons, which are optionally partially chlorinated, and chlorine into a reaction plant maintained at a temperature of from 500 to 700° C. and involving a total residence time of from 5 to 25 s, the amount of chlorine introduced into the reactor being controlled so as to maintain a chlorine concentration of from 3.5 to 6 mol % at the reactor outlet, b) separation of the perchloroethylene produced from the mixture of reaction products obtained in step a), and c) recycling of the residual carbon tetrachloride and chlorine into the reaction plant of step a).

This process not only makes it possible to convert into C$_2$Cl$_4$ the CCl$_4$ generated during the chlorination of hydrocarbons, but also to convert into perchloroethylene a large amount of external CCl$_4$, i.e. CCl$_4$ obtained from other processes. Depending on the operating conditions and the specific geometry of the plant, it is thus possible to achieve conversion into perchloroethylene of amounts of CCl$_4$ which represent more than 60%, for example from 70 to 80%, of the amount of hydrocarbons consumed.

The residence time of the reagents in the reaction plant is generally at least 5 s. Usually, it does not exceed 25 s. Typically, it is between 5 s and 20 s. Preferably, it is between 8 s and 16 s. More preferably, it is greater than 10 s.

The ratios between the various reagents introduced into the reaction plant are controlled such that the HCl/Cl$_2$ molar ratio at the reactor outlet is normally above 8. Preferably, it is greater than 10. As a general rule, this ratio does not exceed 20. Advantageously, it does not exceed 15. It is typically between 8 and 20, preferably between 10 and 15. The Cl$_2$ concentration in the reaction products is itself generally at least 3.5 mol %. Usually, it is not more than 8 mol % and is advantageously less than or equal to 7%. Preferably, it is between 3.5 and 6.5 mol %, more preferably between 3.5 and 6%, most particularly preferably between 3.5 and 5 mol %.

The reaction plant in which the process according to the invention is carried out can consist of one or more reactors, themselves comprising one or more reaction zones. The term reaction zone is intended to denote a zone of the plant in which the temperature is substantially homogeneous, i.e. where temperature differences of greater than about 10° C. are not observed. In a preferred embodiment of the process, the process takes place in several reaction zones.

The operating conditions in the various reaction zones can be optimized as a function of the reactions which take place therein, without directly influencing the operating conditions in the other reaction zones.

According to a preferred embodiment, the process takes place in two separate reaction zones, which are advantageously located in the same reactor. Advantageously, the temperature in the second reaction zone (T$_2$) is lower than the temperature (T$_1$) in the first reaction zone. The temperature difference between the first reaction zone and the second reaction zone (T$_1$–T$_2$) is typically between 10° C. and 150° C., preferably between 20° C. and 100° C. In one specific form of this embodiment of the invention, the second reaction zone is not heated.

The efficacy of the reaction, in particular the degree of conversion of the CCl$_4$ into C$_2$Cl$_4$, is influenced by the temperature difference between the two reaction zones. It has thus been observed that the greater the temperature difference between the first reaction zone and the second reaction zone (T$_1$–T$_2$), the higher the conversion of carbon tetrachloride into perchloroethylene.

In this embodiment, the temperature in the first reaction zone is advantageously between 590° C. and 640° C. and the temperature in the second reaction zone is preferably between 550° C. and 600° C.

Since the reactions which take place in the second reaction zone are largely endothermic, it is advantageous in certain cases to provide a means of heating the second reaction zone of the said plant.

In this embodiment, the residence time of the reagents in each reaction zone is normally at least 1.5 s, and is typically between 2 s and 15 s. Preferably, it is between 2 s and 10 s, it being understood that the total residence time in the reaction plant is always at least 5 s, preferably at least 8 s.

Carbon tetrachloride obtained from an external source and/or recycled carbon tetrachloride can be injected into the first reaction zone of the said plant. Alternatively, or in combination with the injection into the first reaction zone, it is also possible to inject carbon tetrachloride obtained from an external source and/or recycled carbon tetrachloride into the second reaction zone of the said plant. By injecting carbon tetrachloride into the second reaction zone, the production of $C_2Cl_4$ is further favoured.

Figure 2:
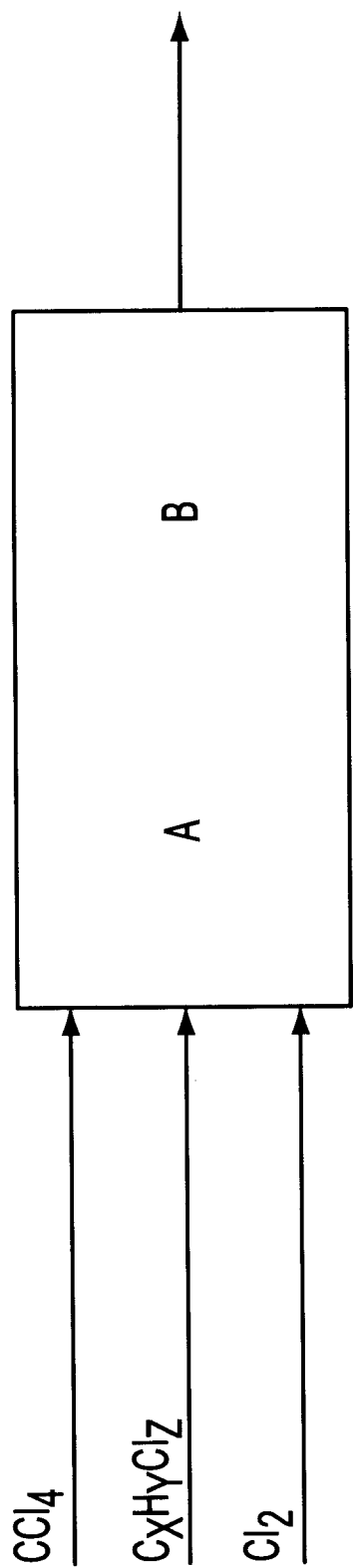

Other advantages and specific features of the invention will emerge from the detailed description of the preferred embodiments described, by way of example, on the basis of the attached drawings, in which:

FIG. 1 is a flow chart of the process for the production of perchloroethylene and of hydrogen chloride by non-catalytic thermal chlorination of hydrocarbons, of partially chlorinated hydrocarbons and/or of mixtures thereof in the presence of carbon tetrachloride and by conversion of carbon tetrachloride into perchloroethylene. FIG. 2 illustrates the preferred embodiment of the invention, in a plant which includes different reaction zones in the same reactor.

The reactor (RTH) is fed with carbon tetrachloride, with hydrocarbons, optionally with partially chlorinated hydrocarbons ($C_xH_yCl_z$) and with chlorine ($C_2$).

After the non-catalytic thermal chlorination of the hydrocarbons and the conversion of the carbon tetrachloride into perchloroethylene and into chlorine, the gaseous mixture is subjected to quenching (Q) and the hydrogen chloride, the chlorine and the heavy by-products (S) are separated from the mixture. The residual gases are then subjected to an additional step of separation of the impurities and to purification (P) in order to obtain perchloroethylene of a desired degree of purity. The residual carbon tetrachloride and the residual chlorine are recycled into the reactor.

FIG. 2 shows an advantageous embodiment of the present process for the production of perchloroethylene, in which two reaction zones are inside the same reactor. The thermal chlorination of $C_1$–$C_3$ hydrocarbons and/or of partially chlorinated $C_1$–$C_3$ hydrocarbons to form carbon tetrachloride and perchloroethylene mainly takes place in the first reaction zone A, while the conversion of the carbon tetrachloride into perchloroethylene and into chlorine mainly takes place in the second reaction zone B which is downstream of zone A.

EXAMPLE

Tests of production of perchloroethylene by non-catalytic thermal chlorination of mixtures of hydrocarbons and of partially chlorinated hydrocarbons in the presence of carbon tetrachloride and by conversion of carbon tetrachloride into perchloroethylene, in a plant which includes at least two separate reaction zones, were carried out.

As starting materials, besides the carbon tetrachloride and the recycled chlorine, the reagents were used in the following proportions:

| Reagent | Flow rate (t/h) |
| --- | --- |
| $C_xH_yCl_z$ | 1.000 |
| External $CCl_4$ | 0.643 |
| Fresh $Cl_2$ | 2.065 |

The average composition of the $C_xH_yCl_z$ was C: 30.0%, H: 3.9% and Cl: 66.1%.

The plant was run under the following conditions:

| | | |
| --- | --- | --- |
| Recycling: | Total flow rate | 3.186 t/h |
| | of which total $CCl_4$ | 2.800 t/h |
| | of which liquid $CCl_4$ | 0.326 t/h |
| Temperatures | Zone A | 615° C. |
| | Zone B | 560° C. |
| $Cl_2$ at reactor outlet | | 3.6 mol % |
| $HCl/Cl_2$ at reactor outlet | | 14.7 mol/mol |
| Residence time (total) | | 10.1 s |
| Pressure | | 1.95 bar abs. |

The following products were removed from the plant:

| Product | Flow rate (t/h) |
| --- | --- |
| $C_2Cl_4$ | 2.061 |
| $CCl_4$ | 0 |
| HCl | 1.421 |
| By-products | 0.226 |

What is claimed is:

1. A process for the production of perchloroethylene from carbon tetrachloride and from $C_1$–$C_3$ hydrocarbons, which are optionally partially chlorinated, this process comprising the steps of:

a) production of perchloroethylene by passing carbon tetrachloride, $C_1$–$C_3$ hydrocarbons, which are optionally partially chlorinated, and chlorine into a reaction plant maintained at a temperature of from 500 to 700° C. and involving a residence time of from 5 to 25 s, the amount of chlorine introduced into the reactor being controlled so as to maintain a chlorine concentration of from 3.5 to 6 mol % at the reactor outlet, b) separation of the perchloroethylene produced from the mixture of reaction products obtained in step a), and c) recycling of the residual carbon tetrachloride and chlorine into the reaction plant of step a).

2. The process according to claim 1, in which the residence time of the reagents in the plant is between 8 and 16 s and the chlorine concentration at the reactor outlet is from 3.5 to 5 mol %.

3. The process according to claim 1, in which the reaction plant includes at least two separate reaction zones in which the temperature in each reaction zone is substantially homogenous.

4. The process according to claim 3, in which the temperature in the second reaction zone ($T_2$) is lower than the temperature ($T_1$) in the first reaction zone.

5. The process according to claim 3, in which the temperature difference between the first reaction zone and the second reaction zone ($T_1$–$T_2$) is between 10° C. and 150° C.

6. The process according to claim 3, in which the temperature difference between the first reaction zone and the second reaction zone ($T_1$–$T_2$) is between 20° C. and 100° C.

7. The process according to claim 3, in which the second reaction zone is not heated.

8. The process according to claim 3, in which carbon tetrachloride obtained from an external source and/or recycled carbon tetrachloride is injected into the first reaction zone of the said plant.

9. The process according to claim 3, in which carbon tetrachloride obtained from an external source and/or recycled carbon tetrachloride is injected into the second reaction zone of the said plant.

10. The process according to claim 3, in which the thermal chlorination of $C_1$–$C_3$ hydrocarbons, which are optionally partially chlorinated, to form carbon tetrachloride and perchloroethylene mainly takes place in the first reaction zone, and the conversion of the carbon tetrachloride into perchloroethylene and into chlorine mainly takes place in the second reaction zone.

11. The process according to claim 1, wherein the residence time is greater than about 8 s.

12. The process according to claim 1, wherein the residence time is greater than about 10 s.

13. The process according to claim 3, wherein the temperature difference between the first reaction zone and the second reaction zone ($T_1$–$T_2$) is between 40° C. and 90° C.

14. The process according to claim 3, wherein the residence time in each reaction zone is greater than about 8 s, and the temperature difference between the first reaction zone and the second reaction zone ($T_1$–$T_2$) is between 40° C. and 90° C.

15. The process according to claim 3, wherein the residence time in each reaction zone is greater than about 10 s, and the temperature difference between the first reaction zone and the second reaction zone ($T_1$–$T_2$) is between 40° C. and 90° C.

* * * * *